(12) United States Patent
Garai et al.

(10) Patent No.: US 11,534,086 B2
(45) Date of Patent: Dec. 27, 2022

(54) LOW-PROFILE WEARABLE MEDICAL DEVICE

(71) Applicant: MEDTRONIC MINIMED, INC., Northridge, CA (US)

(72) Inventors: Ellis Garai, Studio City, CA (US); James E. Burgett, Maple Grove, MN (US); Claire F. Ferraro, Plymouth, MN (US)

(73) Assignee: Medtronic MiniMed, Inc., Northridge, CA (US)

(*) Notice: Subject to any disclaimer, the term of this patent is extended or adjusted under 35 U.S.C. 154(b) by 0 days.

(21) Appl. No.: 17/086,171

(22) Filed: Oct. 30, 2020

(65) Prior Publication Data
US 2022/0133183 A1    May 5, 2022

(51) Int. Cl.
*A61B 5/145*        (2006.01)
*A61B 5/00*         (2006.01)

(52) U.S. Cl.
CPC ........ *A61B 5/14532* (2013.01); *A61B 5/0015* (2013.01); *A61B 5/6833* (2013.01); *A61B 2560/0412* (2013.01)

(58) Field of Classification Search
CPC .............. A61B 5/6833; A61B 5/14503; A61B 5/14865; A61B 5/1473–14735; A61B 2560/0412; A61B 2562/16–166; A61B 5/14248; A61B 5/6831–6833; A61B 2562/164–166; A61B 5/145; A61B 5/1451; A61B 5/14532; A61B 5/14546; A61B 5/1455; A61B 5/1459; A61B 5/1468–14735; A61B 5/1486–14865; A61B 5/6801; A61B 5/6832–68335; A61B 2560/0406–412; H05K 2201/0999
See application file for complete search history.

(56) References Cited

U.S. PATENT DOCUMENTS 4,755,173 A    7/1988    Konopka et al.
5,041,943 A    8/1991    Ilardi et al.
(Continued)

FOREIGN PATENT DOCUMENTS

EP    3120676 B1    3/2018
WO    WO-2011026150 A1 *    3/2011    ........... A61B 5/0002
(Continued)

OTHER PUBLICATIONS

Yanfei Chen, et al., Advanvces in Materials for Recent Low-Profile Implantable Bioelectronics, Mar. 29, 2018, ncbi.hlm.nih.gov/pmc/articles/PMC5951368/.

*Primary Examiner* — Eric F Winakur
*Assistant Examiner* — Alice Ling Zou
(74) *Attorney, Agent, or Firm* — Lorenz & Kopf, LLP

(57) ABSTRACT

Wearable medical devices are provided. An exemplary wearable medical device includes a printed circuit board assembly (PCBA) comprising a dielectric layer having a top surface and conductive features on the top surface of the dielectric layer. Further, the exemplary wearable medical device includes a top housing mounted directly to the top surface of the PCBA. Also, the wearable medical device includes a power source located between the top housing and the PCBA. The top housing and the dielectric layer of the PCBA encapsulates the conductive features and power source and define an outer surface of the wearable medical device.

21 Claims, 4 Drawing Sheets

(56) References Cited

U.S. PATENT DOCUMENTS

| | | |
|---|---|---|
| 5,391,250 A | 2/1995 | Cheney, II et al. |
| 5,462,441 A | 10/1995 | Renn et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,320,128 B1 | 11/2001 | Glovatsky et al. |
| 6,355,021 B1 | 3/2002 | Nielsen et al. |
| 6,379,301 B1 | 4/2002 | Worthington et al. |
| 6,426,484 B1 | 7/2002 | Hembree et al. |
| 6,449,168 B1 | 9/2002 | Soderholm |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 3,024,201 A1 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,585,606 B2 | 11/2013 | McDonald et al. |
| 10,062,958 B2 | 8/2018 | Ganton et al. |
| 10,092,691 B2 | 10/2018 | Searle et al. |
| 10,251,266 B2 | 4/2019 | Seo |
| 10,297,909 B2 | 5/2019 | Kim et al. |
| 2007/0093717 A1* | 4/2007 | Nagar .................... A61B 5/489 |
| | | 600/438 |
| 2007/0123819 A1 | 5/2007 | Mernoe et al. |
| 2010/0160861 A1 | 6/2010 | Causey, III et al. |
| 2010/0305661 A1* | 12/2010 | Crouther ............. A61B 5/6833 |
| | | 604/93.01 |
| 2011/0069459 A1 | 3/2011 | Padiy |
| 2011/0133939 A1* | 6/2011 | Ranganathan ....... A61B 5/0008 |
| | | 340/584 |
| 2014/0163338 A1* | 6/2014 | Roesicke ............. A61B 5/0031 |
| | | 600/309 |
| 2015/0351674 A1 | 12/2015 | Thomas et al. |
| 2016/0149292 A1 | 5/2016 | Ganton et al. |
| 2016/0242654 A1* | 8/2016 | Quinlan ............... A61B 5/7214 |
| 2017/0020456 A1* | 1/2017 | Pace .................. A61B 5/14532 |
| 2017/0290546 A1 | 10/2017 | Antonio et al. |
| 2018/0028824 A1 | 2/2018 | Pivonka et al. |
| 2018/0048056 A1* | 2/2018 | Jow ........................ H01Q 1/38 |
| 2018/0146895 A1* | 5/2018 | Biederman ........ A61B 5/14532 |
| 2018/0301792 A1 | 10/2018 | Park et al. |
| 2019/0038191 A1* | 2/2019 | Parunak ............... A61B 5/1464 |
| 2019/0082968 A1 | 3/2019 | Karnik et al. |
| 2019/0254607 A1 | 8/2019 | Kallback et al. |
| 2019/0374163 A1 | 12/2019 | Faarbaek et al. |
| 2020/0205662 A1 | 7/2020 | Lee et al. |
| 2020/0329557 A1 | 10/2020 | Kim et al. |

FOREIGN PATENT DOCUMENTS

| | | | |
|---|---|---|---|
| WO | WO-2016187536 A1 * | 11/2016 | ........... A61B 5/0022 |
| WO | 2019038751 A1 | 2/2019 | |
| WO | 2019039953 A1 | 2/2019 | |
| WO | 2019239258 A1 | 12/2019 | |

* cited by examiner

LOW-PROFILE WEARABLE MEDICAL DEVICE

TECHNICAL FIELD

The present technology is generally related to wearable medical devices, and more particularly to low-profile wearable medical devices having reduced housing components.

BACKGROUND

The use of wearable medical devices, such as continuous glucose monitor (CGM) devices, is increasing. Wearable medical devices may provide biometric monitoring and reporting relating to the health of a wearer. In many health monitoring applications, a wireless sensor in the wearable medical device is attached directly to or under the user's skin to measure certain data. This measured data can then be utilized for a variety of health-related applications.

Wearable medical devices allow for continuous monitoring of a user's health. However, due to the continuous nature of the monitoring, users are particularly concerned about comfort and the possible obtrusiveness of these devices in certain situations.

Accordingly, it is desirable to provide a low-profile wearable medical device with a reduced height. Also, it may be desirable to provide a wearable medical device with a smaller footprint. In addition, it is desirable to provide a wearable medical device having fewer components. Furthermore, other desirable features and characteristics will become apparent from the subsequent detailed description and the appended claims, taken in conjunction with the accompanying drawings and the foregoing technical field and background.

BRIEF SUMMARY

The subject matter of this disclosure generally relates to a wearable medical device including a printed circuit board assembly (PCBA) comprising a dielectric layer having a top surface and conductive features on the top surface of the dielectric layer, a top housing mounted directly to the top surface of the PCBA, and a power source located between the top housing and the PCBA; wherein the top housing and the dielectric layer of the PCBA encapsulates the conductive features and power source and define an outer surface of the wearable medical device.

In an exemplary wearable medical device, the PCBA has a bottom surface, and the wearable medical device further includes an adhesive on the bottom surface for adhering the wearable medical device to a user's skin.

In an exemplary wearable medical device, the dielectric layer of the PCBA is a rigid member. In another exemplary wearable medical device, the dielectric layer of the PCBA is a flexible member.

In an exemplary wearable medical device, the top housing is a rigid shell. In another exemplary wearable medical device, the top housing is a flexible substrate.

In an exemplary wearable medical device, the top housing is connected directly to the PCBA, thereby forming a continuous peripheral seal therebetween.

An exemplary wearable medical device further includes an antenna electrically connected to the PCBA and located between the PCBA and the top housing. An exemplary antenna is a stamped antenna, additive-manufactured antenna, or flexible electronic trace antenna.

In an exemplary wearable medical device, the top housing has an inner surface facing the PCBA, and the wearable medical device further includes an antenna mounted on the inner surface of the top housing and an antenna connector interconnecting the antenna and the PCBA.

In an exemplary wearable medical device, the top housing has an outer surface and the wearable medical device further includes an antenna mounted on the outer surface of the top housing, a conductive member embedded in the top housing and electrically connected to the antenna, and an antenna connector electrically interconnecting the conductive member and the PCBA. Further, an exemplary antenna on the outer surface of the top housing is located between the top housing and a protective cover.

In one aspect, the present disclosure provides a wearable medical device including a bottom housing, a top housing mounted to the bottom housing and defining an encapsulated volume therebetween, an integrated circuit in the bottom housing, a battery cell located in the encapsulated volume and electrically connected to the integrated circuit, and a sensor having an internal portion located in the encapsulated volume and extending through the bottom housing to an external portion. An exemplary sensor is a glucose sensor.

In an exemplary wearable medical device, the bottom housing has a bottom surface and the wearable medical device further includes an adhesive on the bottom surface for adhering the wearable medical device to a user's skin.

In an exemplary wearable medical device, the top housing is connected directly to the bottom housing, thereby forming a continuous peripheral seal therebetween.

A wearable medical device further includes an antenna located in the encapsulated volume and electrically connected to the integrated circuit.

In an exemplary wearable medical device, the top housing has an inner surface facing the bottom housing, and the wearable medical device further includes an antenna mounted on the inner surface of the top housing and an antenna connector interconnecting the antenna and the integrated circuit.

In an exemplary wearable medical device, the top housing has an outer surface and the wearable medical device further includes an antenna mounted on the outer surface of the top housing; a conductive member embedded in the top housing and electrically connected to the antenna; and an antenna connector electrically interconnecting the conductive member and the integrated circuit. An exemplary antenna on the outer surface of the top housing is located between the top housing and a protective cover.

In another aspect, the disclosure provides a method for fabricating a wearable medical device. The exemplary method includes fabricating an integrated circuit on a dielectric layer, positioning a power source over the dielectric layer, and connecting a top housing to the dielectric layer to define an encapsulated volume between the top housing and the dielectric layer, wherein the integrated circuit and the power source are located in the encapsulated volume.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
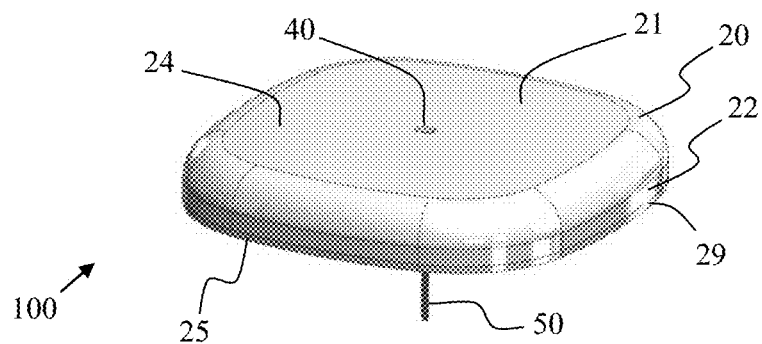
FIG. 1 is a perspective view of a low-profile wearable medical device in accordance with embodiments herein.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

In addition, certain terminology may also be used in the following description for the purpose of reference only, and thus are not intended to be limiting. For example, terms such as "top", "bottom", "upper", "lower", "above", and "below" refer to directions in the drawings to which reference is made. Terms such as "front", "back", "rear", and "side", describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

It should be understood that various aspects disclosed herein may be combined in different combinations than the combinations specifically presented in the description and accompanying drawings.

As described herein, embodiments are provided for reducing the height of wearable medical devices as compared to commercially available devices having interconnected top and bottom housings that encapsulate and protect internal components such as electronics. Embodiments herein provide for reducing the height of wearable medical devices by eliminating the use of a dedicated bottom housing. Instead, embodiments herein may utilize as a bottom housing the dielectric layer of a printed circuit board assembly (PCBA). Specifically, the dedicated bottom housing is replaced with a member that is already needed for operation of the wearable medical device. Further, certain embodiments herein provide for locating the antenna for the medical device at an increased distance from the wearer's skin when being worn.

Figure 2:
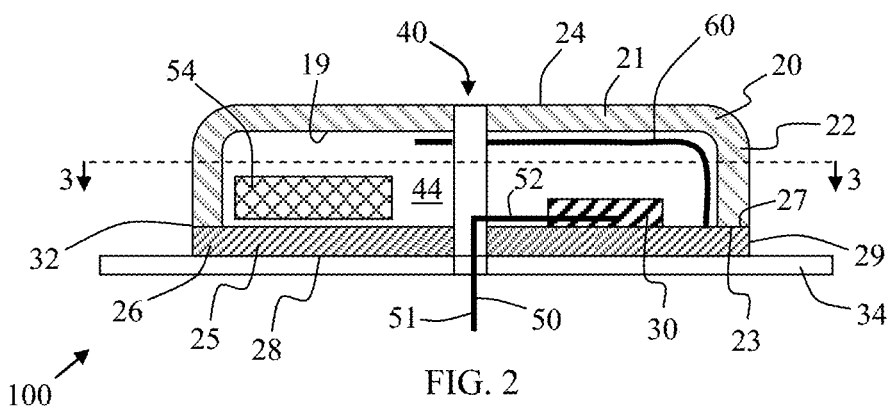
FIG. 2 is a cross-sectional schematic view of the low-profile wearable medical device of FIG. 1, and further including an adhesive layer in accordance with embodiments herein.
Figure 3:
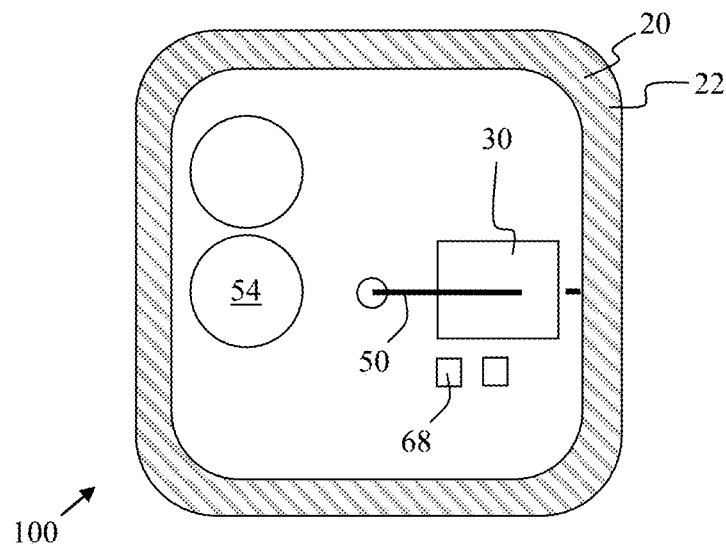
FIG. 3 is an interior schematic view of the low-profile wearable medical device of FIG. 2, taken along line 3-3 in FIG. 2.

Referring to FIG. 1, a perspective view of an exemplary wearable medical device 100 is provided. FIG. 2 is a cross-section view of the exemplary wearable medical device 100 of FIG. 1 (further provided with an adhesive layer). FIG. 3 provides a top view of the internal components of the device 100, taken along line 3-3 in FIG. 2. While wearable medical device 100 may be used for any desired medical purpose, in an exemplary embodiment, the wearable medical device is a continuous glucose monitor (CGM) device. In other embodiments, the wearable medical device 100 may be a single-use or disposable medical device such as an insulin patch pump comprising both medicament-dispensing elements and sensing elements. The wearable medical device 100 may also comprise any one of a number of medical devices wherein form factor and wearability to the patient may be paramount, such as medicament-dispensing patches, health monitoring devices, and the like.

Cross-referencing FIGS. 1-3, it may be seen that the device 100 includes a top housing 20. An exemplary top housing 20 has a horizontally-extending central portion 21 surrounding by a vertical sidewall portion 22 that terminates at a distal end 23. In an exemplary embodiment, the horizontal central and vertical sidewall portions 21 and 22 are integral with one another. As shown, the top housing has an outer surface 24 and an inner-facing underside 19 or inner surface.

FIGS. 2-3 illustrate internal components of the device 100. As shown, the device 100 includes a printed circuit board assembly (PCBA) 25 comprising a dielectric layer 26 having a top surface 27 and a bottom surface 28, and end surfaces 29. As shown, conductive features 30 are located on and/or under the top surface 27 of the dielectric layer 26, as is common for integrated circuit fabrication. The conductive features 30 may be deposited and/or etched as conductive traces and may form integrated circuit components such as transistors, diodes, resistors, capacitors, inductors, and the like. Exemplary conductive features 30 are formed as integrated circuits according to conventional fabrication processing, such that the dielectric layer 26 may include a plurality of dielectric sublayers, and conductive layers formed therein and overlying the top surface 27 define the conductive features 30. In an exemplary embodiment, the conductive features 30 or a portion thereof define a system-on-a-chip (SoC).

In an exemplary embodiment, the top housing 20 is mounted over and directly sealed to the PCBA 25, and specifically to the dielectric layer 26. As shown most clearly in FIG. 2, the distal end 23 of the top housing 20 is directly sealed to the dielectric layer 26 at or adjacent the peripheral edge of the top surface 27. As a result, a continuous peripheral seal 32 is formed at the interface of the distal end 23 of the top housing 20 and the top surface 27 of the dielectric layer 26 of the PCBA 25. In exemplary embodiments, the top housing 20 may be sealed to the top surface 27 by radiofrequency (RF) welding, ultrasound welding, or an adhesive.

As further shown in FIG. 2 (and not shown in FIG. 1), an exemplary device 100 may further include an adhesive patch 34 or adhesive layer 34 adhered to the bottom surface 28 of the dielectric layer 26. During wear of the device 100 by a user, the adhesive layer 34 adheres the device 100 to the user's skin.

As shown in FIGS. 1-3, the device 100 is provided with a central opening 40 extending from the top housing 20 through the PCBA 25. The central opening 40 may allow a needle or probe to position a distal end of a sensor described below at a desired location for use, such as in or under the wearer's skin. The central opening 40 is sealed, such as by a tubular wall. With the top housing 20 connected to the PBCA 25 and the central opening 40 sealed, an internal volume 44 is defined and encapsulated between the top housing 20 and the PCBA 25. As a result, internal components such as electronics are protected. In other words, the encapsulated internal volume 44 is waterproof under normal conditions, i.e., typical environmental pressures and temperatures, so that components located within the internal volume 44 are protected during use. As shown, the device 100 is formed with an outer surface defined by the outer surface 24 of the top housing 20 and by the bottom surface 28 and end surfaces 29 of the dielectric layer 26 of the PCBA 25.

As shown in FIGS. 1-3, the device 100 includes a sensor 50 or sensor assembly. A distal portion 51 or external portion 51 of the sensor 50 is located within the central opening 40 and extends out of the device 100. A proximal portion 52 or internal portion 52 of the sensor 50 is located in the internal volume 44 of the device 100 and is electrically connected to the PCBA 25 and conductive features 30 for operation of the device 100. For user of the device 100, a probe may be inserted through the central opening 40 to position the distal portion 51 of the sensor 50 under a user's skin. While not shown, o-rings may be located around the central opening 40 at the interface with the sensor 50 to further ensure that the internal volume 44 is completely sealed.

Embodiments of sensors 50 provided herein use biological elements to convert a chemical analyte in a matrix into a detectable signal. In certain embodiments, a sensor 50 of the type presented here is designed and configured for subcutaneous operation in the body of a patient. An exemplary sensor 50 is a glucose sensor. The sensor 50 includes electrodes that are electrically coupled to a suitably configured electronics module that applies the necessary excitation voltages and monitors the corresponding electrical responses (e.g., electrical current, impedance, or the like) that are indicative of physiological characteristics of the body of the patient. For the embodiment described here, the sensor 50 may include a working electrode, reference electrode and counter electrode. An exemplary working electrode has includes a platinum layer, an analyte sensing layer over the platinum layer and including a catalyst or reagent or enzyme, such as glucose oxidase (GOx), a protein layer over the analyte sensing layer, an adhesion promoting layer over the protein layer, and an overlying selective permeable membrane. The working electrode may work according to the following chemical reactions:

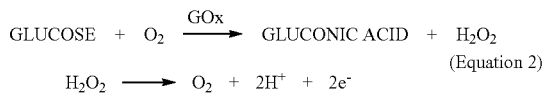

(Equation 1)

(Equation 2)

The glucose oxidase (GOx) is provided in the sensor 50 and is encapsulated by a semipermeable membrane adjacent the working electrode. The semipermeable membrane allows for selective transport of glucose and oxygen to provide contact with the glucose oxidase. The glucose oxidase catalyzes the reaction between glucose and oxygen to yield gluconic acid and hydrogen peroxide (Equation 1).

The H2O2 then contacts the working electrode and reacts electrochemically as shown in Equation 2 under electrocatalysis by the working electrode. The resulting current can be measured by a potentiostat. These reactions, which occur in a variety of oxidoreductases known in the art, are used in a number of sensor designs.

When the sensor electrodes are placed at a subcutaneous location at a selected site in the body of a user, the sensor electrodes are exposed to the user's bodily fluids such that they can react in a detectable manner to the physiological characteristic of interest, e.g., blood glucose level. In certain embodiments, the sensor electrodes may include one or more working electrodes, counter electrodes, and reference electrodes. For the embodiments described here, the sensor electrodes employ thin film electrochemical sensor technology of the type used for monitoring blood glucose levels in the body. Further description of flexible thin film sensors of this general type are found in U.S. Pat. No. 5,391,250, entitled METHOD OF FABRICATING THIN FILM SENSORS, which is herein incorporated by reference. In other embodiments, different types of implantable sensor technology, such as chemical based, optical based, or the like, may be used.

In FIGS. 2 and 3, the device 100 is shown to further include a power source 54 located in the internal volume 44, i.e., between the top housing 20 and the PCBA 25. An exemplary power source 54 is a battery cell, such as a single coin cell or double coin cell as shown in FIG. 3. The power source 54 is electrically connected to the PCBA 25 and conductive features 30 to power operation of the device 100.

As further shown in FIGS. 2 and 3, the device 100 includes an antenna 60, such as an RF antenna. An exemplary antenna 60 is a stamped antenna, an additive-manufactured ("3D-printed) antenna, or folded flex PCB trace antenna. An exemplary antenna 60 is electrically connected to the PCBA 25 or conductive features 30. Performance of the antenna 60 may be improved by increasing the distance between the antenna 60 and the user's body. Therefore, as shown in FIG. 2, the antenna 60 may extend upward to the inner surface 19 of the top housing 20 at the central portion 21 and extend horizontally away from the vertical sidewall portion 22 toward the center of the device 100.

As indicated in FIG. 3, the device 100 may further include external components 68. Exemplary external components 68 are antennae, connectors, communication ports, or power ports, capacitors, resistors, inductors, amplifiers, comparators, and the like. In exemplary embodiments, the external components 68 are electrically connected to the PCBA 25 and/or conductive features 30. As is known, the wearable medical device 100 may include additional components that are not illustrated or described herein but are common in such devices.

In the embodiment of FIGS. 1-3, the top housing 20 may be a rigid member such as a rigid shell. For example, the top housing 20 may be formed from a hard plastic material such as polycarbonate, ABS, polyether ether ketone (PEEK), polypropylene (PP), and the like.

Further, in the embodiment of FIGS. 2 and 3, the dielectric layer 26 of the PCBA is a rigid member or a flexible member. For a rigid member, the dielectric layer 26 may be ceramic material or fiberglass, i.e., glass-reinforced epoxy laminate material, such as for example FR4 composite material. For a flexible member, i.e., a flex PCBA, the dielectric layer 26 may be polyimide or other suitable material.

Figure 4:
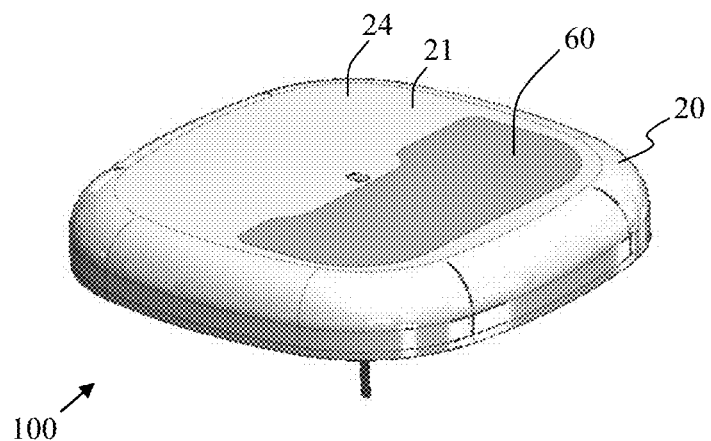
FIG. 4 is a perspective view of a low-profile wearable medical device in accordance with embodiments herein.
Figure 5:
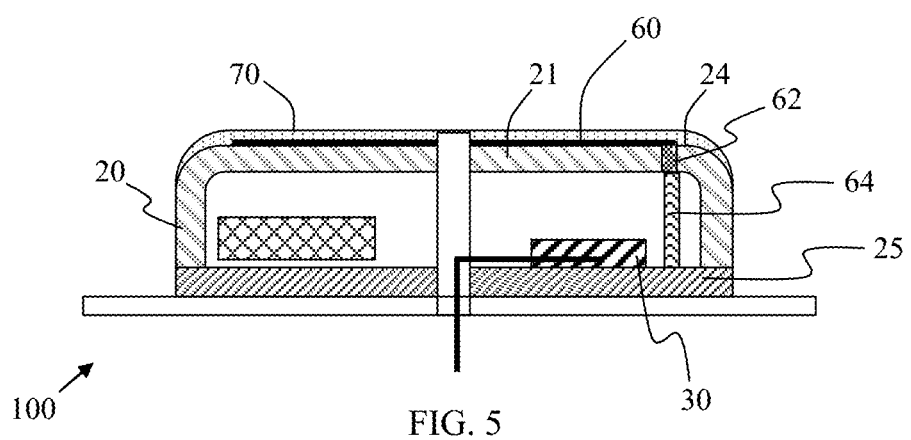
FIG. 5 is a cross-sectional schematic view of the low-profile wearable medical device of FIG. 4.

Referring now to FIGS. 4 and 5, another exemplary embodiment of wearable medical device 100 is provided.

FIG. 4 provides a perspective view and FIG. 5 provides a cross-sectional view of the device 100. The device 100 of FIGS. 4-5 is similar to the device 100 of FIGS. 1-3, but for the design of the antenna 60. Specifically, in FIGS. 4 and 5, the antenna 60 is located over or on the outer surface 24 of the central portion 21 of the top housing 20. Further, as shown in FIG. 5, the top housing 20 is formed with an aperture in which a conductive member 62 is embedded. Also, the device 100 includes an antenna connector 64, such as a pogo pin or a spring leaf biased to an extended orientation for electrical contact with the conductive member 62. For operation of the antenna 60, the antenna connector 64 is electrically connected to the PCBA 25 or conductive features 30, the conductive member 62 is electrically connected to the antenna connector 64, and the antenna 60 is electrically connected to the conductive member 62.

As illustrated in FIG. 5, the wearable medical device 100 further includes a protective cover 70. As shown, the protective cover 70 lies over the antenna 60 such that the antenna 60 is encapsulated between the protective cover 70 and the top housing 20. An exemplary protective cover 70 may be an adhesive layer or other material suitable for waterproofing the antenna 60.

Figure 6:
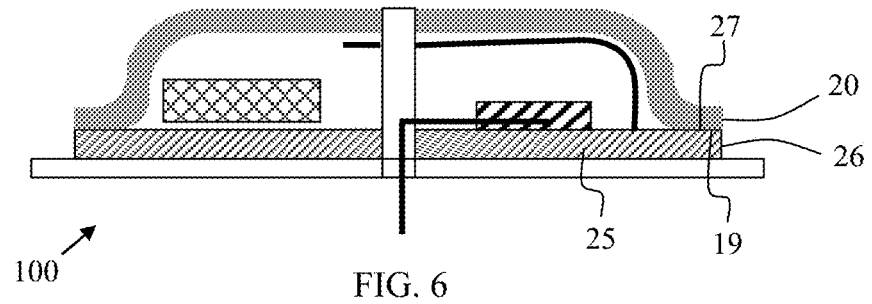
FIG. 6 is a cross-sectional schematic view of a low-profile wearable medical device in accordance with embodiments herein.

FIG. 6 illustrates another exemplary embodiment of the wearable medical device 100. In FIG. 6, the top housing 20 is flexible. Specifically, the top housing 20 is formed from a flexible material or substrate, such as polyimide or other suitable material.

As shown, the structure of the embodiment of FIG. 6 is similar to that of FIG. 2 but for the interconnection between the top housing 20 and the PCBA 25. Specifically, in FIG. 6, the inner surface 19 of the top housing 20 is directly sealed to the dielectric layer 26 of the PCBA 25 at or adjacent the peripheral edge of the top surface 27. As a result, a continuous peripheral seal 32 is formed at the interface of the top housing 20 and the top surface 27 of the dielectric layer 26 of the PCBA 25. In exemplary embodiments, the top housing 20 may be sealed to the top surface 27 by radiofrequency (RF) welding, ultrasound welding, or an adhesive.

Figure 7:
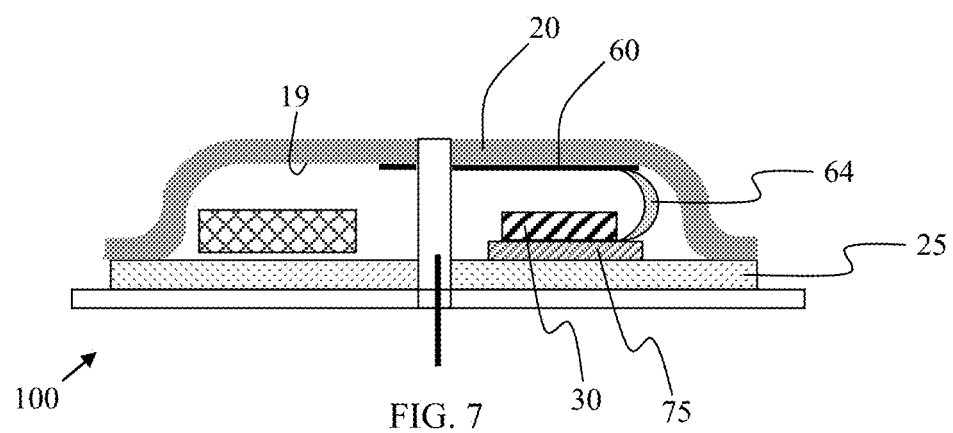
FIG. 7 is a cross-sectional schematic view of a low-profile wearable medical device in accordance with embodiments herein.

FIG. 7 illustrates another exemplary embodiment of the wearable medical device 100. In FIG. 7, the top housing 20 is flexible and is sealed to the PCBA 25, similar to the structure of FIG. 6. As shown in FIG. 7, the antenna 60 is located on the inner surface 19 of the top housing 20. In an exemplary embodiment, the antenna 60 is formed as an electronic trace on the inner surface 19 of the top housing 20.

The embodiment of FIG. 7 further includes a second PCBA 75. For example, PCBA 25 may be flexible and PCBA 75 may be rigid. Various electronic components may be formed in PCBA 25 or PCBA 75 and interconnected electrically. As further shown in FIG. 7, the device 100 includes an antenna connector 64, such as a spring leaf biased to an extended orientation for electrical contact with the antenna 60. For operation of the antenna 60, the antenna 60 is electrically connected to the antenna connector 64 and the antenna connector 64 is electrically connected to the PCBA 25, PCBA 75, or conductive features 30.

Figure 8:
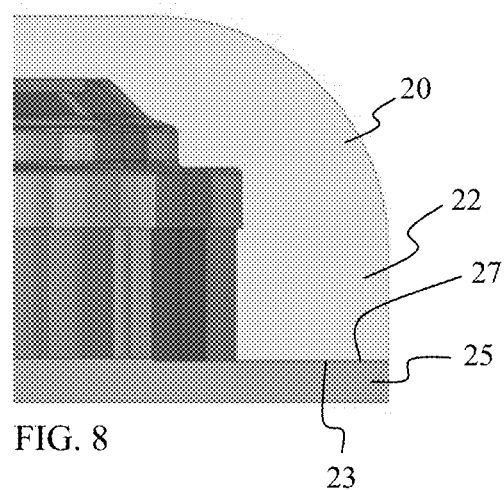
FIGS. 8-10 are cross-sectional schematic views of portions of low-profile wearable medical devices illustrating the connection between the top housing and the PCBA in accordance with embodiments herein.
Figure 9:
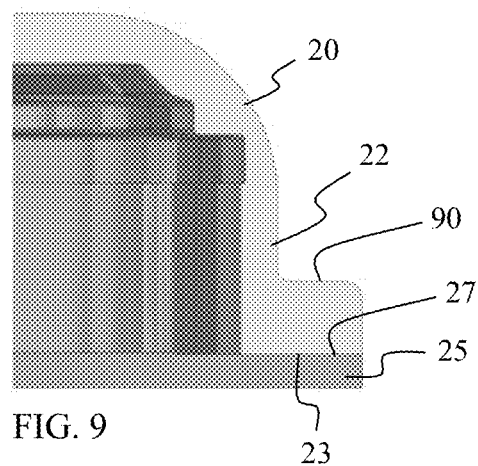
Figure 10:
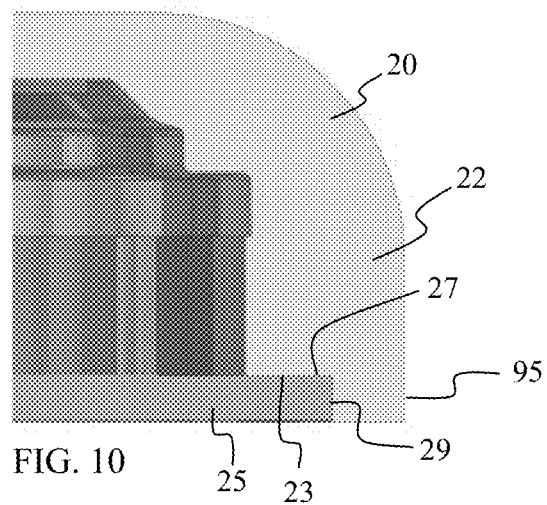

FIGS. 8-10 illustrate various structures for interconnecting the top housing 20 and the PCBA 25. In FIG. 8, the distal end 23 of the vertical sidewall 22 of the top housing 20 contacts and is sealed to the top surface 27 of the PCBA 25.

Similar to FIG. 8, in FIG. 9 the distal end 23 of the vertical sidewall portion 22 of the top housing 20 contacts and is sealed to the top surface 27 of the PCBA 25. However, in FIG. 9, the top housing 20 is formed with a step surface 90.

As a result, a countering force may be applied to surface 90 and to PCBA 25 when sealing the distal end 23 to the top surface 27.

In FIG. 10, the top housing 20 extends over the end surface 29 of the PCBA 25. As a result, a force can be applied to the location 95 of the top housing 20 when sealing the top housing 20 to the end surface 29 and to the top surface 27 of the PCBA 25

While the embodiments of the wearable medical device 100 of FIGS. 1-10 have been described as lacking a bottom housing, it is contemplated that the PCBA 25 may be considered to be a bottom housing and that the wearable medical device 100 lacks a dedicated bottom housing, i.e., an additional and separate element without function other than to encapsulate the internal components of the wearable medical device 100. With such an understanding, in FIGS. 1-10, the top housing 20 is mounted directly to a bottom housing 25 and integrated circuits or conductive feature 30 are formed in and/or directly on the bottom housing 25.

In addition to the wearable medical device 100, methods for fabricating wearable medical devices are disclosed. In an exemplary method, integrated circuits or conductive features 30 are fabricated over, on and/or in a dielectric layer 26. Further, a power source 54 and portion of a sensor 50 are positioned over the dielectric layer 26. The method also includes connecting a top housing 20 to the dielectric layer 26 to define an encapsulated internal volume 44 between the top housing 20 and the dielectric layer 26. In the exemplary method, the integrated circuit 30, power source 54, and portion of sensor 50, as well as other internal features, are located in the encapsulated internal volume 44. The wearable medical device 100 may be positioned at a desired location on a wearer's skin and adhered thereto, such as with adhesive layer 34. Further, a probe or needle may be advanced through the central opening 40 in the wearable medical device 100, to place the distal portion 51 of the sensor 50 at a desired location, such as under the skin.

As described herein, a wearable medical device 100 is provided with a reduced height by eliminating a dedicated bottom housing from the structure of the device 100. Instead, a dielectric layer 26 of a PCBA 25 serves as the bottom housing to which the top housing is sealed. Further, embodiments herein provide for locating the antenna from the skin at an increased distance despite the elimination of a dedicated bottom housing. For example, in certain embodiments, the antenna may be located in the internal volume 44 immediately below the inner surface 19 of the top housing 20, located on the inner surface 19 of the top housing 20, or located in or on the outer surface 24 of the top housing 20.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A wearable medical device comprising:
   a printed circuit board assembly (PCBA) comprising a
      dielectric layer having a top surface and conductive features on the top surface of the dielectric layer, wherein the dielectric layer has a bottom surface defining a bottom plane;
a top housing mounted directly to the top surface of the PCBA, wherein a continuous peripheral seal is formed between the top housing and the PCBA, and wherein the top housing has an upper surface located above the bottom plane and terminates at a bottom edge located in or above the bottom plane; and
a power source located between the top housing and the PCBA; wherein the top housing and the dielectric layer of the PCBA encapsulate the conductive features and power source and define an outer surface of the wearable medical device;
wherein an adhesive is located directly on the bottom surface of the dielectric layer for adhering the wearable medical device to a user's skin.

2. The wearable medical device of claim 1 wherein the top housing extends laterally to an outer periphery, and wherein the adhesive extends laterally from under the top housing to outside the periphery of the top housing.

3. The wearable medical device of claim 1 wherein the medical device has an outermost lateral surface extending from the bottom surface of the dielectric layer to the upper surface of the top housing, wherein the outermost lateral surface is comprised of only the dielectric layer and the top housing.

4. The wearable medical device of claim 1 wherein the bottom edge is located in the bottom plane.

5. The wearable medical device of claim 1 wherein the top housing is formed with a central portion surrounded by a substantially vertical sidewall portion that is mounted directly to the top surface of the PCBA, and wherein the sidewall portion includes a substantially horizontal step surface for applying a downward force thereon to seal the wearable medical device to a user's skin.

6. The wearable medical device of claim 1 wherein the top housing is a flexible substrate extending from a first end to a second end and having a bottom side and a top side opposite of the bottom side, wherein the bottom side of the flexible layer defines the bottom edge and is mounted directly to the top surface of the dielectric layer, wherein the PCBA is a flexible PCBA, and wherein the wearable medical device further comprises a rigid PCBA mounted to the top surface of the dielectric layer.

7. The wearable medical device of claim 1 wherein the PCBA has an outer side edge, and wherein the top housing is connected directly to the top surface and the outer side edge of the PCBA, thereby forming the continuous peripheral seal therebetween.

8. The wearable medical device of claim 1 further comprising an antenna electrically connected to the PCBA and located between the PCBA and the top housing, wherein the antenna comprises a vertical portion connected to the PCBA and a horizontal portion distanced from and extending in a direction parallel to the PCBA.

9. The wearable medical device of claim 6 further comprising:
an antenna located between the PCBA and the top housing, wherein the antenna is a flexible electronic trace antenna, and wherein the antenna is located within a plane distanced from and parallel to the PCBA; and
an antenna connector biased to an extended orientation to electrically connect the antenna and the rigid PCBA.

10. The wearable medical device of claim 1 wherein the top housing and the PCBA surround an encapsulated volume, and wherein a vertical line through a central portion of the wearable medical device passes directly from the adhesive to the PCBA, directly from the PCBA to the encapsulated volume, and directly from the encapsulated volume to the top housing.

11. The wearable medical device of claim 1 wherein the wherein the outer surface of the wearable medical device consists of the PCBA and the top housing.

12. The wearable medical device of claim 1 wherein the bottom edge of the top housing defines a device footprint area, and wherein the adhesive completely covers the device footprint area.

13. A wearable medical device comprising:
a printed circuit board assembly (PCBA) comprising a dielectric layer serving as a bottom housing for the wearable medical device and an integrated circuit, wherein the PCBA has a central region surrounded by a peripheral region;
an adhesive located directly on the bottom surface of the dielectric layer for adhering the wearable medical device to a user's skin;
a top housing having a horizontally-extending central portion surrounded by a sidewall portion, wherein the sidewall portion is mounted directly to the peripheral region of the PCBA at an annular interface, and wherein an encapsulated volume is defined within the horizontally-extending central portion, the sidewall and the PCBA; and
internal components located in the encapsulated volume, including a battery cell located in the encapsulated volume and electrically connected to the integrated circuit; a sensor having an internal portion located in the encapsulated volume and extending through the bottom housing to an external portion; and an antenna on the horizontally-extending central portion of the top housing,
wherein a vertical line through a central portion of the wearable medical device passes directly from the adhesive to the PCBA, directly from the PCBA to the encapsulated volume, and directly from the encapsulated volume to the top housing.

14. The wearable medical device of claim 13 wherein the wearable medical device terminates in an upward direction at the top housing.

15. The wearable medical device of claim 13 wherein a continuous peripheral seal is formed between the PCBA and the top housing.

16. The wearable medical device of claim 13 wherein the wearable medical device consists of the PCBA, the adhesive, the top housing, and the internal components.

17. The wearable medical device of claim 13 wherein the top housing is flexible, wherein the horizontally-extending central portion of the top housing has an inner surface facing the bottom housing, wherein the antenna is mounted on the inner surface of the horizontally-extending central portion of the top housing; and wherein the wearable medical device further comprises a flexible antenna connector biased to an extended orientation to electrically connect the antenna and the integrated circuit.

18. The wearable medical device of claim 17, wherein the PCBA is flexible, wherein the wearable medical device further comprises a rigid PCBA mounted to the top surface of the dielectric layer, and where in the flexible antenna connector connects the antenna and the rigid PCBA.

19. The wearable medical device of claim 18 wherein the top housing is a flexible substrate extending from a first end to a second end and having a bottom side and a top side opposite of the bottom side, wherein the bottom side of the flexible layer defines the bottom edge and is mounted directly to the top surface of the dielectric layer.

20. The wearable medical device of claim 13 wherein the sensor is a glucose sensor.

21. A method for fabricating a wearable medical device, the method comprising:
   fabricating an integrated circuit on a dielectric layer;
   positioning a power source over the dielectric layer;
   connecting a top housing to the dielectric layer at a continuous annular seal to define an encapsulated volume between the top housing and the dielectric layer, wherein the integrated circuit and the power source are located in the encapsulated volume; and
   fixing an adhesive layer to a bottom surface of the dielectric layer, wherein the adhesive extends laterally beyond an outer periphery of the top housing and laterally beyond an outer periphery of the dielectric layer.

\* \* \* \* \*